(12) United States Patent
Chau et al.

(10) Patent No.: US 8,187,820 B2
(45) Date of Patent: May 29, 2012

(54) DETECTION METHOD USING NANOAGGREGATE-EMBEDDED BEADS AND SYSTEM THEREOF

(75) Inventors: Laikwan Chau, Chiayi (TW); Tzyy-Schiuan Yang, Chiayi County (TW); Ping-Ji Huang, Kaohsiung County (TW); Tai-Tsung Lin, Nantou County (TW)

(73) Assignee: National Chung Cheng University, Chia-Ye (TW)

( * ) Notice: Subject to any disclaimer, the term of this patent is extended or adjusted under 35 U.S.C. 154(b) by 0 days.

(21) Appl. No.: 13/134,417

(22) Filed: Jun. 7, 2011

(65) Prior Publication Data

US 2011/0256578 A1     Oct. 20, 2011

Related U.S. Application Data

(62) Division of application No. 12/291,927, filed on Nov. 14, 2008, now abandoned.

(60) Provisional application No. 60/996,387, filed on Nov. 15, 2007.

(51) Int. Cl.
*G01N 33/53* (2006.01)

(52) U.S. Cl. .......................................... 435/7.1; 436/518

(58) Field of Classification Search .......................... None
See application file for complete search history.

(56) References Cited

U.S. PATENT DOCUMENTS

| 7,776,547 B2 | 8/2010 | Roth et al. | |
|---|---|---|---|
| 2002/0044972 A1* | 4/2002 | Davis et al. | 424/486 |
| 2003/0059820 A1 | 3/2003 | Do-Vinh et al. | |
| 2005/0147963 A1* | 7/2005 | Su et al. | 435/5 |
| 2006/0046313 A1 | 3/2006 | Roth et al. | |
| 2006/0100524 A1 | 5/2006 | Lucassen et al. | |
| 2008/0102036 A1 | 5/2008 | Poss et al. | |

OTHER PUBLICATIONS

Westcott et al. (Langmuir et al. 1998, vol. 14, p. 5396-5401).*
Lu et al. Reference (Nano Letters 2002 vol. 2, p. 183-186).*
Gong JL et al, "Novel dye-embedded core-shell nanoparticles as surface-enhanced Raman scattering tags . . . ", Analytica Chimica Acta vol. 564, Issue 2, Apr. 6, 2006, pp. 151-157.
Kim JH et al., "Naoparticle Probes With Surface Enhanced Raman Spectroscopic Tags for Cellular Cancer Targeting", Anal. Chem. Oct. 1, 2006; 78 (19); p. 6967-73.

* cited by examiner

*Primary Examiner* — Jacob Cheu
(74) *Attorney, Agent, or Firm* — Hudak, Shunk & Farine Co. LPA

(57) ABSTRACT

The invention discloses a detection method using nanoaggregate-embedded beads and system thereof, which are characterized in that the nanoaggregate of Raman dye and metal nanoparticles is coated by an inorganic oxide to form a nanoaggregate-embedded bead, and which is then conjugated with a probe molecule to form a sensor bead. The Raman spectra of the product formed by binding of the sensor bead and an analyte in a sample is detected for determining whether the analyte exists in the sample. In embodiment, the pH of the solution of metal nanoparticles is controlled to keep at 10, and the concentration of the Raman dye is controlled to keep between $1\times10^{-6}$ M and $2\times10^{-6}$ M for reducing the size of the nanoaggregate.

12 Claims, 9 Drawing Sheets

US 8,187,820 B2

DETECTION METHOD USING NANOAGGREGATE-EMBEDDED BEADS AND SYSTEM THEREOF

CROSS REFERENCE

This is a division of U.S. application Ser. No. 12/291,927, filed Nov. 14, 2008 for DETECTION METHOD USING NANOAGGREGATE-EMBEDDED BEADS AND SYSTEM THEREOF, which claims priority to U.S. Provisional Patent Application No. 60/996,387 filed Nov. 15, 2007.

BACKGROUND OF THE INVENTION (a) Field of the Invention

The present invention is related to a detection method using nanoaggregate-embedded beads and system thereof, and more particularly to a technical field of coating the nanoaggregate of Raman dye and nanoparticles with silica or metal oxide to form a shell.

(b) Description of the Prior Art

Fluorescence is commonly applied to optical barcoding or spectroscopic tagging scheme, fluorescent tags especially. For example, the fluorescence can be applied in the molecular genetic biotechnology of DNA sequencing and DNA microarrays. Some fluorescence molecules are used to detect certain ion by fluorescence probe in host cell to provide the cell physiology status and activity. At the same time, green fluorescent protein (GFP) can fuse with target gene that causes disease. Therefore, the field of the medical science can realize the function and mechanism of activity of target gene that causes disease in the host cell.

However, the shortcomings of the fluorescent tags may result in photo-bleaching and peak overlapping in multiplex bio-detection.

SUMMARY OF THE INVENTION

Therefore, one of the objectives of the present invention is to provide a detection method using nanoaggregate-embedded beads and system thereof, in order to solve the disadvantage of using fluorescence label in multiplex bio-detection in prior art.

To achieve the above-mentioned objective, the present invention provides a detection method using nanoaggregate-embedded beads, and the detection method comprises the following steps of:

a) adding a Raman dye into a solution of metal nanoparticles to generate nanoaggregates, and coating the nanoaggregates with an inorganic oxide to obtain nanoaggregate-embedded beads;

b) conjugating the nanoaggregate-embedded bead with a probe molecule to form a sensor bead;

c) detecting Raman spectra of the product formed by binding of the sensor bead and an analyte in a sample; and d) determining whether the analyte exists in the sample according to the Raman spectra.

Besides, the present invention provides a detection system using nanoaggregate-embedded beads, which comprises a light source, a first detection unit and a second detection unit. The light source is capable of emitting a light to a product formed by binding of an analyte and a nanoaggregate-embedded bead conjugated with a probe molecule. The first detection unit is capable of detecting a first signal from the product, and the second detection unit capable of detecting a second signal from the product, so that the simultaneous detection of multiple analytes existing in a sample or analytes bound at different locations on a surface of array biochip can be achieved by reading the first signal and the second signal.

The detection method using nanoaggregate-embedded beads and system thereof in accordance with the present invention can have one or more of the following advantages:

(1) the nanoaggregate-embedded beads conjugating with different probe molecules or including different Raman dyes inside can be applied to multiplex detection.

(2) the initial selection for biomolecular recognition can be performed according to scattering or absorption of light by the noble metal nanoparticles.

(3) the problem of photo-bleaching and peak overlapping resulted from usage of the fluorescent tags in multiplex bio-detection can be solved.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

Figure 1:
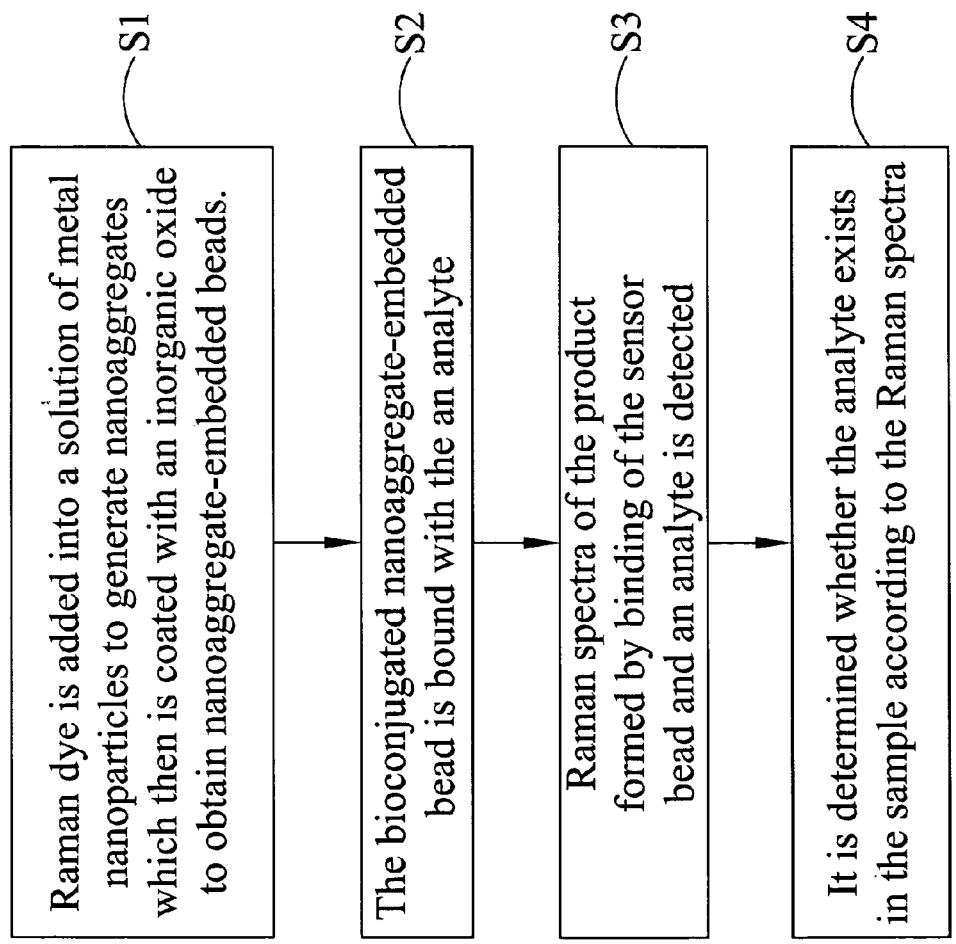
FIG. 1 illustrates a flowchart of the detect method using nanoaggregate-embedded beads in accordance with the present invention.

FIG. 1 illustrates a flowchart of the detection method using nanoaggregate-embedded beads in accordance with the present invention. The method comprises the following steps.

In step S1, a Raman dye is added into a solution of metal nanoparticles to generate nanoaggregates which then are coated with an inorganic oxide to obtain nanoaggregate-embedded beads. Preferably, the inorganic oxide is comprised of silica or metal oxide, and the metal nanoparticle is comprised of gold nanoparticle or silver nanoparticle.

Besides, the size of the nanoaggregate can be controlled by changing the pH of the solution containing metal nanoparticles, and the pH of the solution is preferable in a range from 7 o 12. Preferably, the average size of the nanoaggregate is ranged from 20 nm to 80 nm, and number of nanoparticles included in the nanoaggregate is between 2 and 7.

Preferably, the Raman dye can be a dye molecule with isothiocyanate (—N=C=S), thiol, or amine group, multiple sulfur atoms or multiple nitrogen atoms, such as TRITC (tetramethyl-rhodamine-5-isothiocyanate), XRITC (X-rhodamine-5-isothiocyanate), XRITC (X-rhodamine-6-isothiocyanate), DTDC (3,3'-diethylthiadicarbocyanine iodine), R6G (rhodamine 6G).

The dye molecule with isothiocyanate (—N=C=S) or thiol and the molecule having multiple sulfur atoms can bind with the metal nanoparticle chemically to form stronger bond. However, the amine group is not the functional group which can bind with the metal nanoparticle chemically, so a coating assistant agent, 3-mercaptopropyl)-trimethoxysilane (MPTMS), must be added to assist the R6G to keep adsorbed on the metal nanoparticle surface and form a weaker bond.

In the embodiment, the coating assistant agent can be added during the coating of inorganic oxide when weakly binding Raman dye, such as R6G, is used. Typically, an optimized quantity of R6G was added to the gold nanoparticle solution first. After 15 minutes reaction, MPTMS is added before silica encapsulation, in order to assist R6G to keep binding with the gold nanoparticles.

The concentration of MPTMS is related to the size of the nanoaggregate-embedded bead coated with silica. When the concentration of MPTMS becomes higher, the size of the nanoaggregate-embedded bead becomes smaller. However, R6G would not bind with the gold nanoparticle if the concentration of MPTMS is too high. Preferably, the concentration of MPTMS is ranged from $0.1 \times 10^{-6}$ M to $5 \times 10^{-6}$ M.

Besides, the silica coating process is preferably performed without adding MPTMS when a strongly binding Raman dye, such as XRITC TRITC and DTDC, is used. In this case, the coating agent, such as TEOS (Tetraethylorthosilica) or TMOS (Tetramethylorthosilica), is added stepwise in several aliquots into the reaction solution at least every 15 minutes, and the ammonia is also added into the reaction solution to enhance the silica encapsulation effect. Preferably, the concentration of ammonia is ranged from 0.4 wt.-% to 1.6 wt.-%.

Next, in step S2, the bioconjugated nanoaggregate-embedded bead is bound with an analyte in a sample. In the embodiment, a first probe molecule can be conjugated on the surface of the nanoaggregate-embedded bead to form a sensor bead first, and such sensor bead is then bound with an epitope of the analyte.

In other embodiment, a first probe molecule is conjugated on the surface of the nanoaggregate-embedded bead to form a sensor bead and a second probe molecule is conjugated on the surface of the array biochip. The analyte then binds with the second probe molecule first, and the sensor bead is used to bind with analyte directly, or compete with the analyte which has bound with the second probe molecule in advance. Preferably, the analyte can be a molecule that binds with the first probe molecule.

Preferably, the first probe molecule can be a chemoreceptor, an antibody, an antigen, a lectin, a hormone receptor, a nucleic acid, or a carbohydrate, and the second probe molecule can be an antibody, an antigen or a nucleic acid corresponding to the first probe molecule.

Finally, in step S3 Raman spectra of the product formed by binding of the sensor bead and an analyte in a sample is detected, and then in step S4 it is determined whether the analyte exists in the sample according to the Raman spectra.

Besides, for performing the simultaneous detection of multiple analytes existing in a sample or analytes bound at different locations on a surface of array biochip, the user can use the nanoaggregate-embedded beads conjugating with different probe molecules or including different Raman dyes inside the sensor beads for multiplex detection. When particular nanoaggregate-embedded beads bind with the analytes, the simultaneous detection of multiple analytes existing in a sample or analytes bound at different locations on a surface of array biochip can be achieved by reading the Raman spectra.

Figure 2:
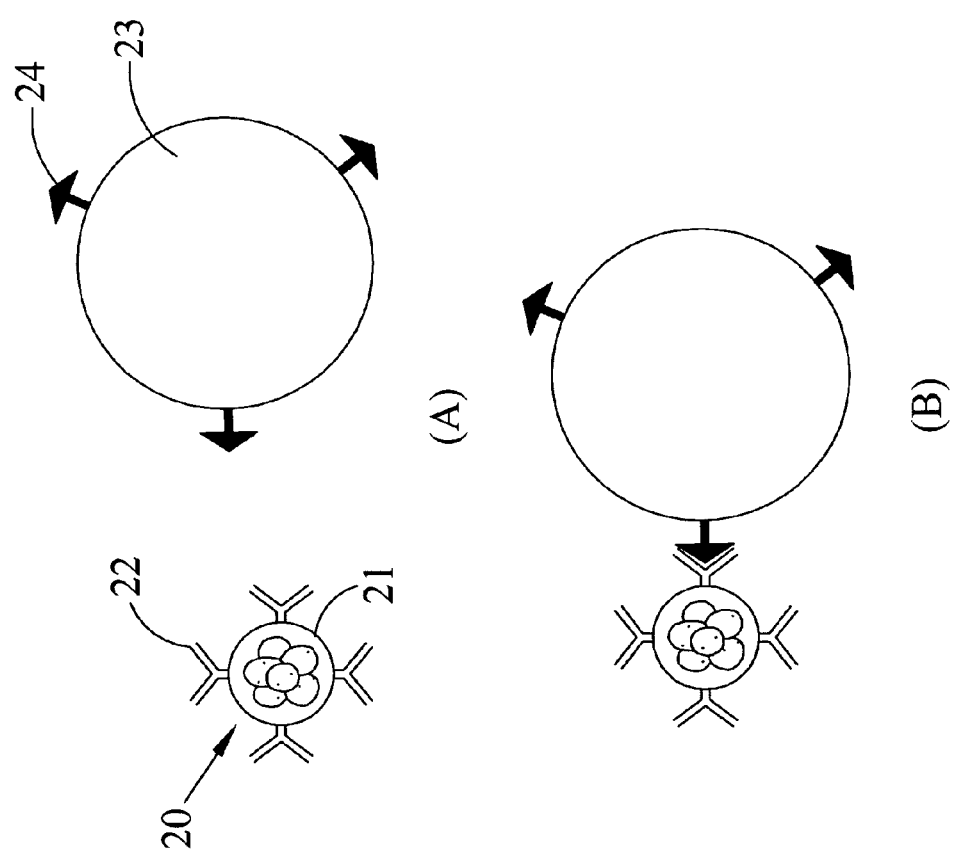
FIG. 2 illustrates a first embodiment schematic view of binding of nanoaggregate-embedded bead and analyte in accordance with the present invention.

FIG. 2 illustrates a first embodiment schematic view of binding of nanoaggregate-embedded bead and analyte in accordance with the present invention. In this embodiment, the surface of nanoaggregate-embedded bead 21 is conjugated with multiple antibodies 22 thereon to form a sensor bead 20, and the surface of microorganism 23 has multiple antigens 24 thereon. By binding of the antibody 22 and antigen 24 of the microorganism 23, the sensor bead 20 can bind with the microorganism 23 for further detection process. Therefore, the sensor bead 20 can be used to detect whether the microorganism 23 exists in the sample.

Figure 3:
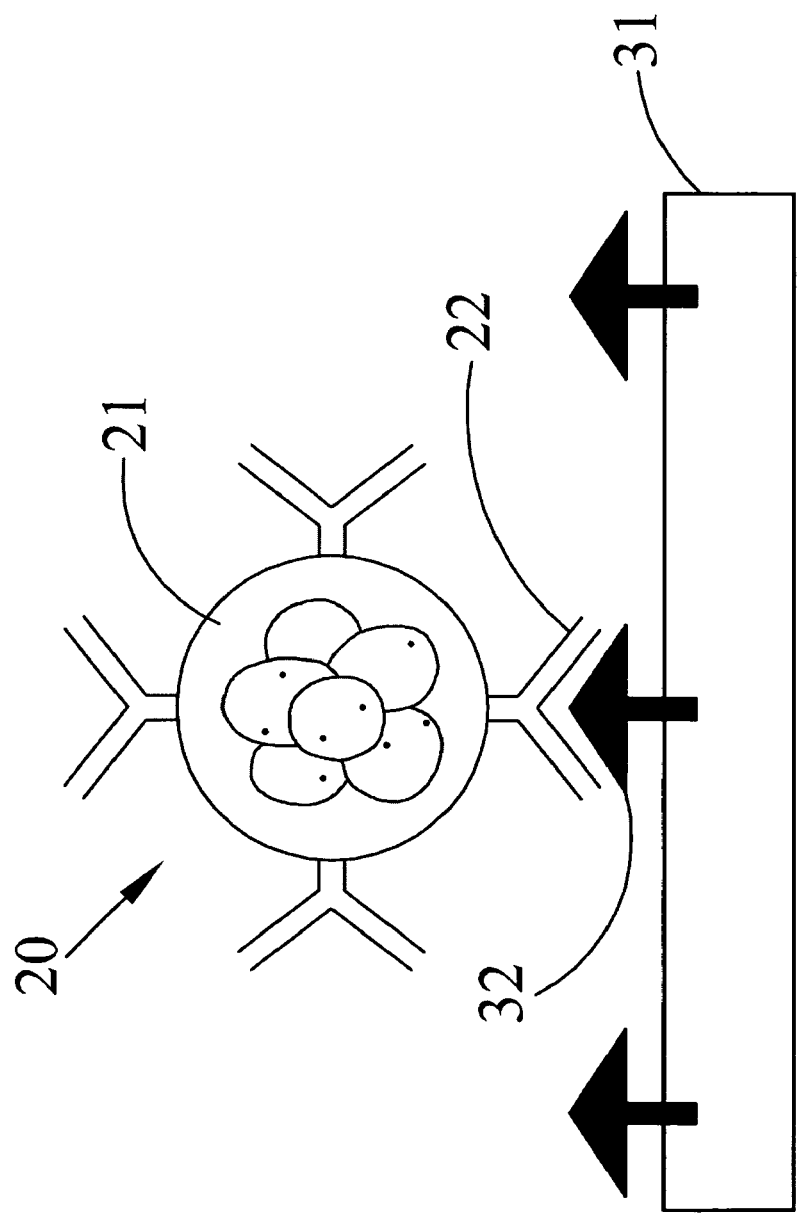
FIG. 3 illustrates a second embodiment schematic view of binding of nanoaggregate-embedded bead and analyte in accordance with the present invention.

FIG. 3 illustrates a second embodiment schematic view of binding of nanoaggregate-embedded bead and analyte in accordance with the present invention. In this embodiment, the surface of nanoaggregate-embedded bead 21 is conjugated with multiple antibodies 22 thereon to form a sensor bead 20, and the surface of the substrate 31 is conjugated with multiple antigens 32 in advance. By binding of the antibody 22 and antigen 32, the sensor bead 20 can bind with the substrate 31 for further detection process. For example, the substrate can be an array biochip so that the simultaneous detection of analytes bound at different locations on a surface of the array biochip can be achieved by reading the Raman spectra from the product formed by binding of antigen 32 and the sensor bead 20. Preferably, the substrate can also be bio-sample or cell.

Figure 4:
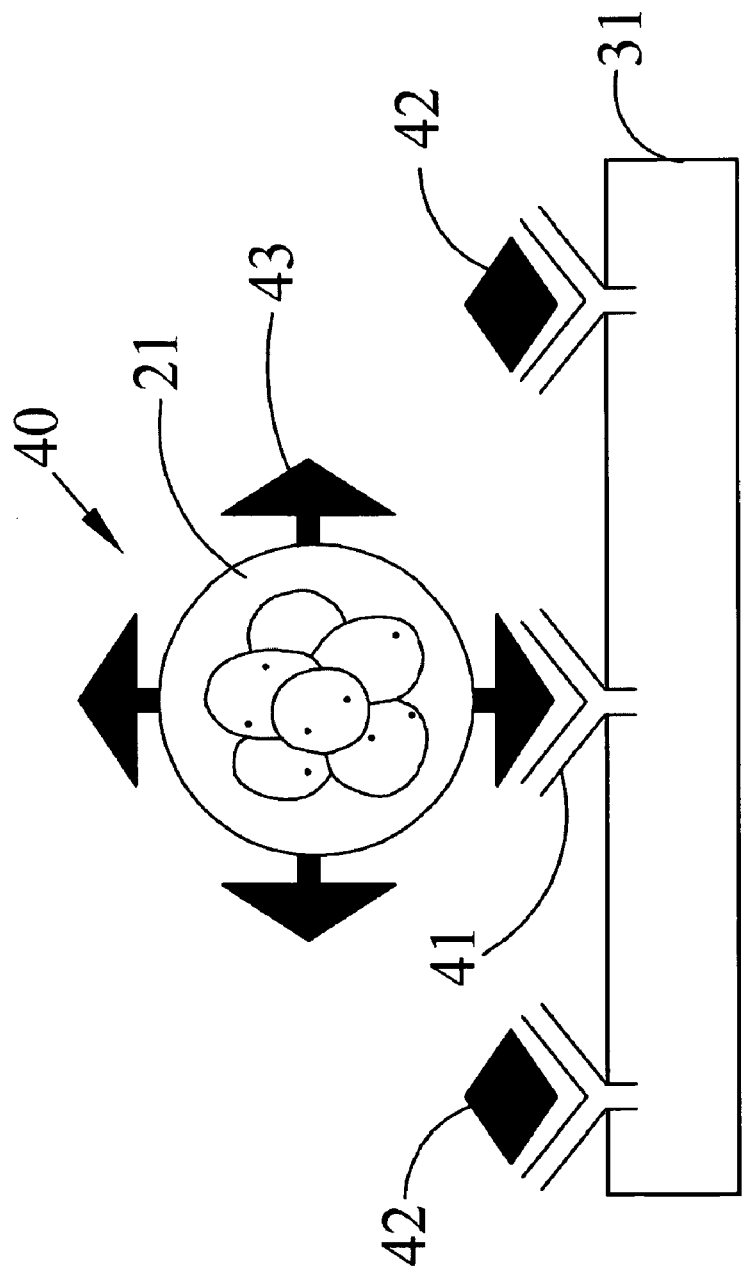
FIG. 4 illustrates a third embodiment schematic view of binding of nanoaggregate-embedded bead and analyte in accordance with the present invention.

FIG. 4 illustrates a third embodiment schematic view of binding of nanoaggregate-embedded bead and analyte in accordance with the present invention. In this embodiment, the surface of nanoaggregate-embedded bead 21 is conjugated with multiple first antigens 43 thereon to form a sensor bead 40, and the surface of the substrate 31 is conjugated with multiple antibodies 41 in advance. The relationship between the first antigen 43 and the second antigen 42, which serves as an analyte in sample, is a competition relationship. As shown in FIG. 4, the sensor bead 40 competes with the second antigen 42 for binding with antibody 41. Therefore, the amount of the analyte can be detected indirectly by using the sensor bead 40.

Figure 5:
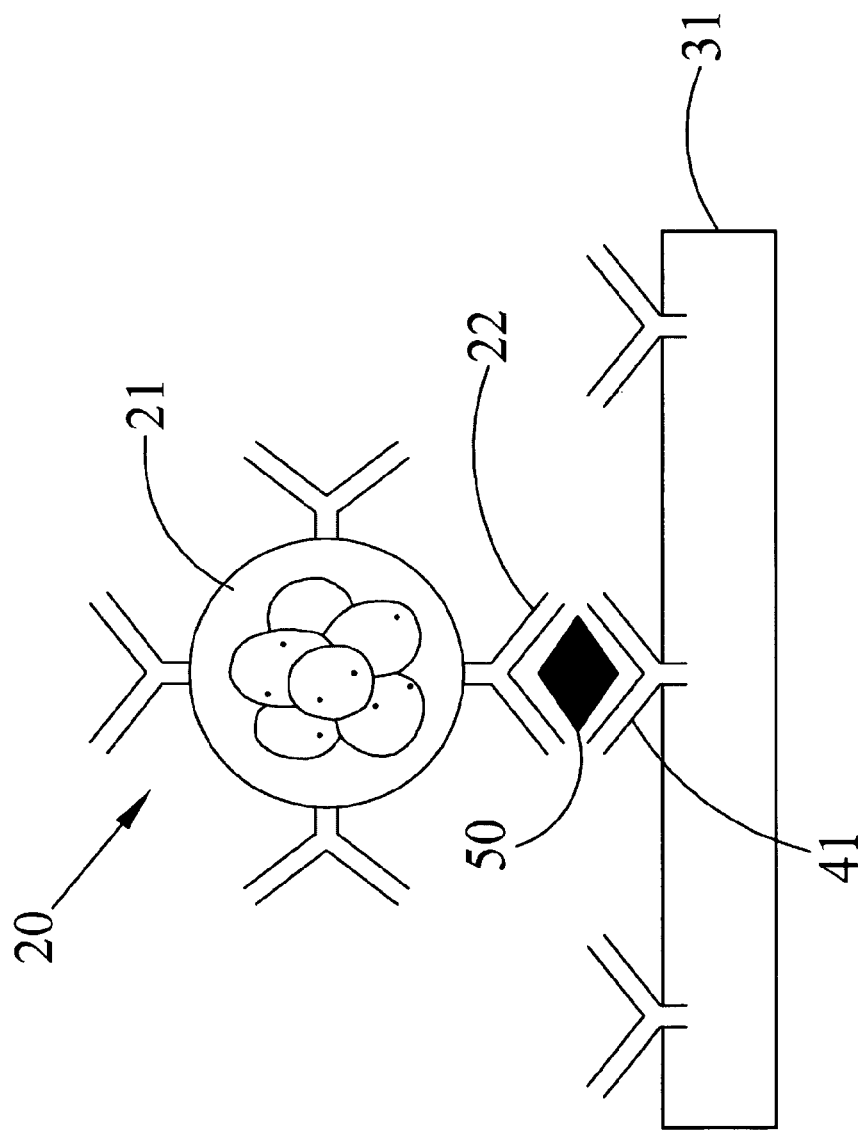
FIG. 5 illustrates a fourth embodiment schematic view of binding of nanoaggregate-embedded bead and analyte in accordance with the present invention.

FIG. 5 illustrates a fourth embodiment schematic view of binding of nanoaggregate-embedded bead and analyte in accordance with the present invention. In this embodiment, the surface of nanoaggregate-embedded bead 21 is conjugated with multiple antibodies 22 thereon to form a sensor bead 20, and the surface of the substrate 31 is conjugated with multiple antibodies 41 in advance. The antibody 22 and the antibody 41 can bind together via antigen 50, which serves as an analyte in sample, so that the nanoaggregate-embedded bead 21 can capture the antigen 50 and bind with the substrate 31. Therefore, the amount of antigens 50 in a sample can be measured by reading the Raman spectra from the product formed by binding of antigen 50 and the sensor bead 20.

Figure 6:
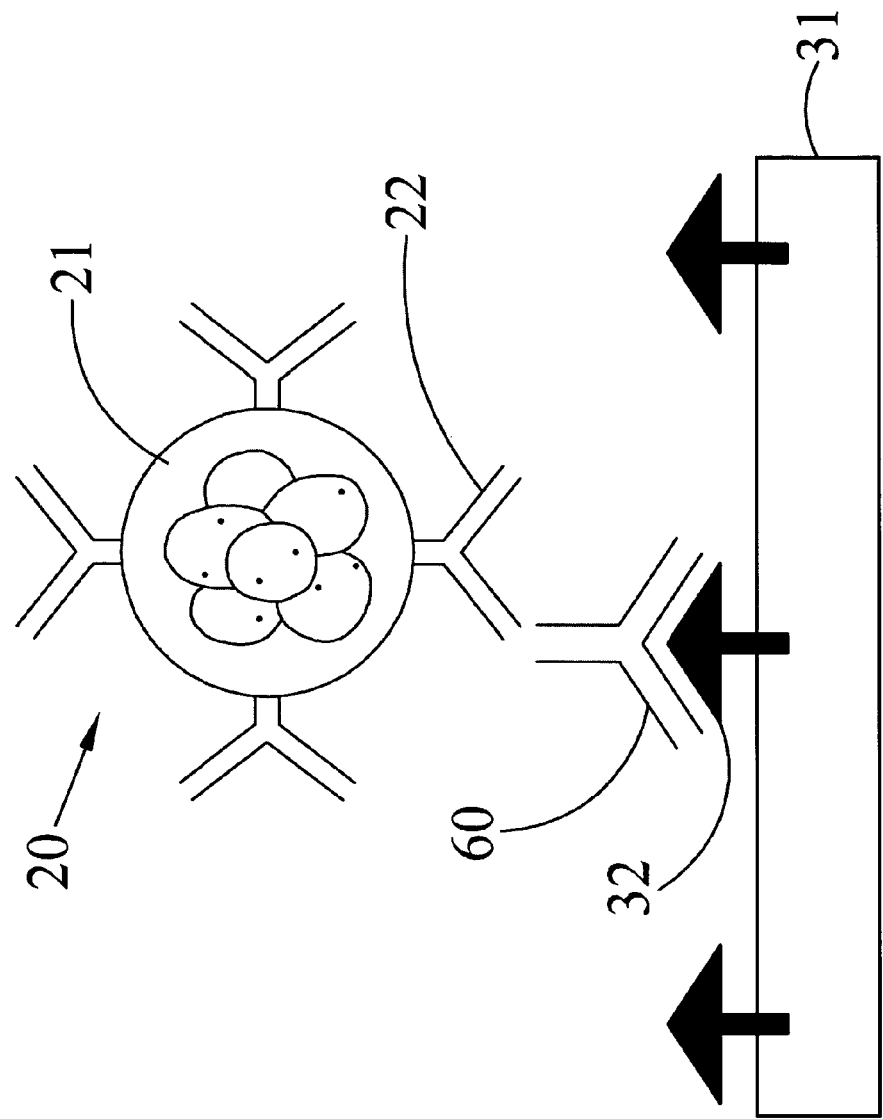
FIG. 6 illustrates a fifth embodiment schematic view of binding of nanoaggregate-embedded bead and analyte in accordance with the present invention.

Similarly, as shown in FIG. 6, the antibody conjugated on the surface of the substrate 31 can be replaced by antigen 32, so that sensor bead 20 can bind with the substrate 31 via antibody 60, and the amount of antibody 60 in a sample can be measured by reading the Raman spectra.

Figure 7:
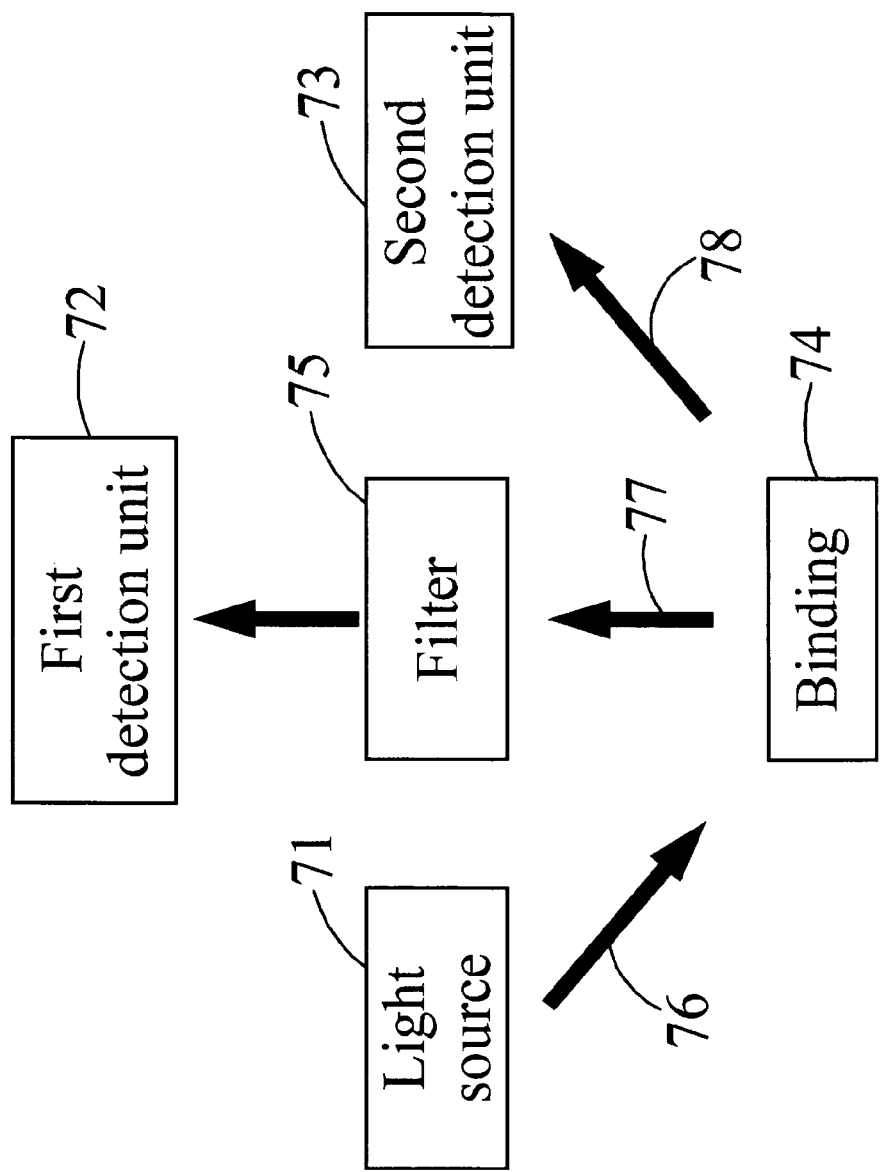
FIG. 7 illustrates a block diagram of a detection system using nanoaggregate-embedded beads in accordance with the present invention.

FIG. 7 illustrates a block diagram of a detection system using nanoaggregate-embedded beads in accordance with the present invention. The detection system comprises a light source 71, a first detection unit 72 and a second detection unit 73. The light source is capable of emitting a light 76 to a product 74, formed by binding of an analyte and a nanoaggregate-embedded bead conjugated with a probe molecule, and then a first signal and second signal are generated from the product 74. The first signal is filtered by a filter 75 before being inputted to the first detection unit 72. The second signal is inputted to the second detection unit 73. The simultaneous detection of multiple analytes existing in a sample or analytes bound at different locations on a surface of array biochip can be achieved by reading spectra of the first signal 77 and the second signal 78.

Preferably, the light source is a laser with wavelength ranged from 500 nm to 800 nm, and the first detection unit 72 can be a Raman spectrometer, and the second detection unit can be a photodetector. Preferably, the analyte can be an antibody, an antigen, a cytokine, hormone, a growth factor, a neuropeptide, a hemoglobin, a plasma protein, an amino acid, a vitamin, nucleic acid, a carbohydrate, a glycoprotein, a fatty acid, a phosphatidic acid, a sterol, a antibiotic, a cell, a toxin, a virus or a bacterium. The first signal 77 is preferred to be a Raman signal, and the second signal 78 is preferred to be a scattering light or transmission light. Preferably, the filter can be a Raman filter.

Figure 8:
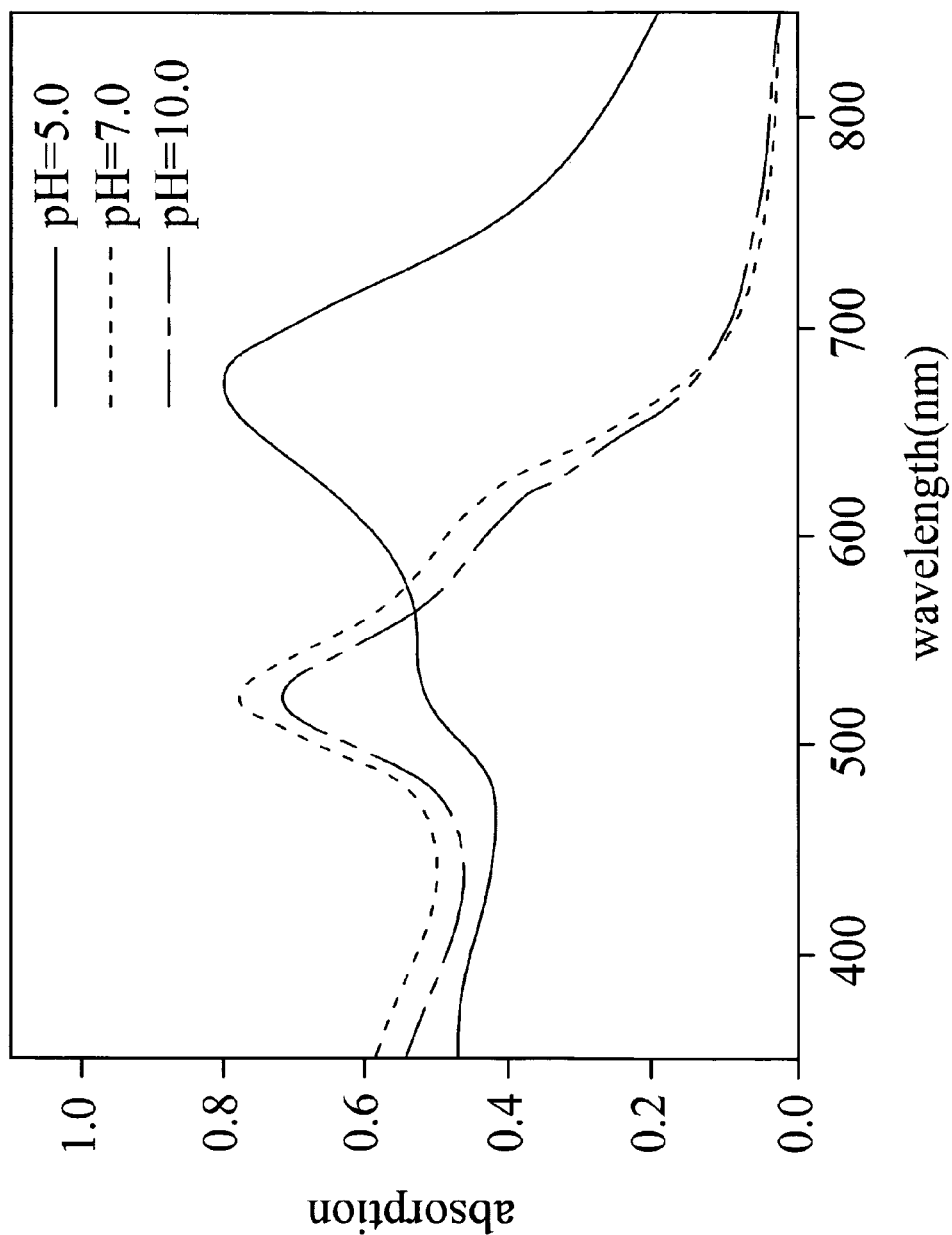
FIG. 8 illustrates UV-vis absorption spectra of gold nanoaggregates while the gold nanoparticle solutions are at various pH values and mixed with XRITC at a final concentration of $1.14 \times 10^{-6}$ M.

FIG. 8 illustrates UV-vis absorption spectra of gold nanoaggregates while the gold nanoparticle solutions are at various pH values and mixed with XRITC at a final concentration of $1.14 \times 10^{-6}$ M. Compared with the spectrum of the solution with pH 5, it can be observed clearly that spectra of solutions ranging from pH 7 to pH 12, preferably with pH 7 or 10 just have a shoulder appears at above 600 nm. This indicates that the gold nanoaggregates have smaller size and are suitable to be a label. Therefore, the manner of changing the pH of the solution of metal nanoparticles to control the size of the aggregate, which is disclosed by the present invention, can enhance the detection effect efficiently.

Figure 9:
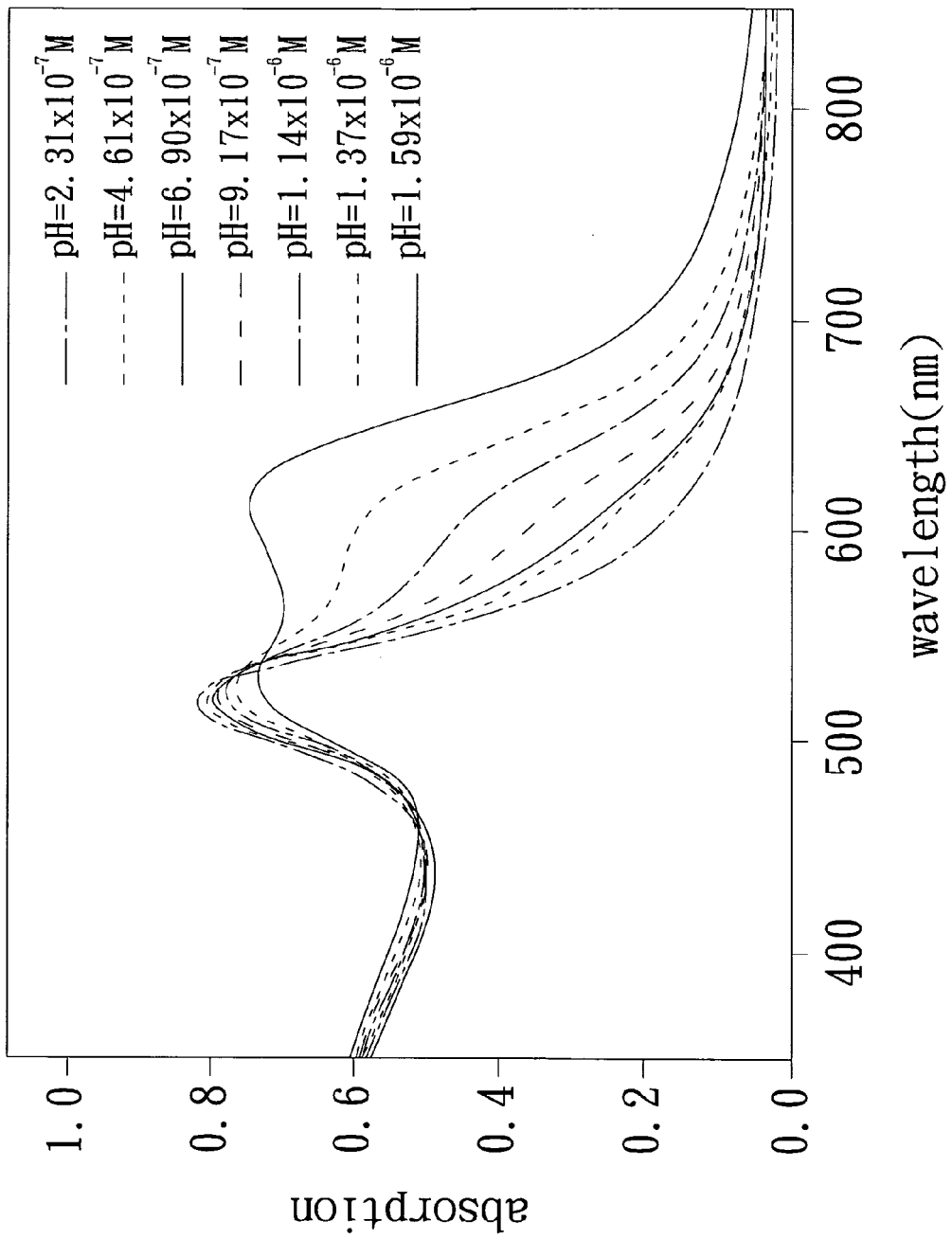
FIG. 9 illustrates the UV-vis absorption spectra of gold nanoaggregates while the gold nanoparticle solutions at pH 10.0 are mixed with XRITC at a final concentration from $1.59 \times 10^{-6}$ M to $2.31 \times 10^{-7}$ M.

FIG. 9 illustrates the UV-vis absorption spectra of gold nanoaggregates while the gold nanoparticle solutions at pH 10.0 are mixed with XRITC at a final concentration from $2.31 \times 10^{-7}$ M to $1.59 \times 10^{-6}$ M. It can be observed clearly that just a shoulder appears at above 600 nm while the concentration of the XRITC is below $1.37 \times 10^{-6}$ M. This indicates that the gold nanoaggregates have smaller size and are suitable to be a label. Therefore, the manner of keeping the concentration of the Raman dye at between $0.1 \times 10^{-6}$ M to $5 \times 10^{-6}$ M, preferably between $1 \times 10^{-6}$ M to $2 \times 10^{-6}$ M to control the size of the aggregate, which is disclosed by the present invention, can enhance the detection effect efficiently.

In accordance with the patent statutes, the best mode and preferred embodiment have been set forth; the scope of the invention is not limited thereto, but rather by the scope of the attached claims.

What is claimed is:

1. A detection method using nanoaggregate-embedded beads, comprising steps of:
    a) Adding a Raman dye into a solution of metal nanoparticles and varying a pH value of the solution of metal nanoparticles and controlling a concentration of the Raman dye to generate nanoaggregates, wherein a size of each of the nanoaggregates is adjusted by varying the pH value of the solution of metal nanoparticles, wherein the pH value of the solution of metal nanoparticles is ranged from 7 to 12, and the concentration of the Raman dye is controlled to be between $0.1 \times 10^{-6}$ M and $5 \times 10^{-6}$ M, and the average size of the nanoaggregate is ranged from 20 nm to 80 nm;
    b) coating the nanoaggregates with an inorganic oxide to obtain nanoaggregate-embedded beads;
    c) conjugating the nanoaggregate-embedded bead with a probe molecule to form a sensor bead;
    d) detecting Raman spectra of the product formed by binding of the sensor bead and an analyte in a sample; and
    e) determining whether the analyte exists in the sample according to the Raman spectra.

2. The detection method of claim 1, wherein the inorganic oxide comprises silica or metal oxide.

3. The detection method of claim 1, wherein the Raman dye is comprised of an organic molecule with isothiocyanate, thiol, or amine group, multiple sulfur atoms or multiple nitrogen atoms.

4. The detection method of claim 1, wherein the metal nanoparticles comprise gold metal nanoparticle or silver metal nanoparticle.

5. The detection method of claim 1, wherein the probe molecule comprises a chemoreceptor, an antibody, an antigen, a lectin, a hormone receptor, a nucleic acid, or a carbohydrate.

6. The detection method of claim 1, wherein the step (b) further comprises a step of:
    adding a coating agent for performing the coating of inorganic oxide.

7. The detection method of claim 6, wherein the coating agent comprises Tetraethylorthosilica or Tetramethylorthosilica.

8. The detection method of claim 6, further comprising a step of:
    adding an ammonia, wherein the concentration of the ammonia is controlled between 0.4 wt.-% and 1.6 wt.-%.

9. The detection method of claim 1, wherein an assistant-agent-based step can be implemented between the step (a) and the step (b) by adding a coating assistant agent for assisting the coating of inorganic oxide.

10. The detection method of claim 9, wherein the coating assistant agent comprises (3-mercaptopropyl)-trimethoxysilane.

11. The detection method of claim 10, wherein the concentration of the (3-mercaptopropyl)-trimethoxysilane which relates to a size of the nanoaggregate-embedded bead is ranged between $0.1 \times 10^{-6}$ M and $5 \times 10^{-6}$ M.

12. The detection method of claim 1, wherein the analyte comprises an antibody, an antigen, a cytokine, a hormone, a growth factor, a neuropeptide, a hemoglobin, a plasma protein, an amino acid, a vitamin, a nucleic acid, a carbohydrate, a glycoprotein, a fatty acid, a phosphatidic acid, a sterol, an antibiotic, a cell, a toxin, a virus or a bacterium.

* * * * *